(12) United States Patent
Jain et al.

(10) Patent No.: US 9,408,814 B2
(45) Date of Patent: Aug. 9, 2016

(54) MODIFIED RELEASE DOSAGE FORM COMPRISING DESVENLAFAXINE OR SALTS THEREOF

(75) Inventors: Girish Kumar Jain, Delhi (IN); Premchand Dalichandji Nakhat, Yavatmal (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 0 days.

(21) Appl. No.: 13/582,440

(22) PCT Filed: Mar. 21, 2011

(86) PCT No.: PCT/IB2011/051160
§ 371 (c)(1),
(2), (4) Date: Nov. 12, 2012

(87) PCT Pub. No.: WO2011/121475
PCT Pub. Date: Oct. 6, 2011

(65) Prior Publication Data
US 2013/0059917 A1    Mar. 7, 2013

(30) Foreign Application Priority Data
Mar. 31, 2010  (IN) .................. 1099/MUM/2010

(51) Int. Cl.
| A61K 31/137 | (2006.01) |
| A61P 15/00 | (2006.01) |
| A61P 25/00 | (2006.01) |
| A61P 25/08 | (2006.01) |
| A61P 25/16 | (2006.01) |
| A61P 25/18 | (2006.01) |
| A61P 25/22 | (2006.01) |
| A61P 25/24 | (2006.01) |
| A61P 3/04 | (2006.01) |
| A61K 9/20 | (2006.01) |
| A61K 9/28 | (2006.01) |
| A61K 47/24 | (2006.01) |

(52) U.S. Cl.
CPC ............. *A61K 31/137* (2013.01); *A61K 9/2054* (2013.01); *A61K 9/2866* (2013.01); *A61K 47/24* (2013.01)

(58) Field of Classification Search
CPC ... A61K 9/2054; A61K 47/24; A61K 31/137; A61K 9/2866
See application file for complete search history.

(56) References Cited

U.S. PATENT DOCUMENTS

| 2005/0175698 | A1 | 8/2005 | Diorio et al. | |
| 2007/0281020 | A1* | 12/2007 | Ulloa et al. | ................... 424/468 |
| 2008/0188567 | A1 | 8/2008 | Huang et al. | |
| 2008/0220064 | A1* | 9/2008 | Ramesh | ............... A61K 9/2018 |
| | | | | 424/485 |
| 2009/0018208 | A1* | 1/2009 | Hadfield et al. | ............... 514/653 |

FOREIGN PATENT DOCUMENTS

| EP | 2119696 A1 | 11/2009 |
| EP | 2191822 A1 | 6/2010 |
| WO | WO2006/104791 A1 | 10/2006 |
| WO | WO 2007/011619 A2 | 1/2007 |
| WO | WO2009/075677 A1 | 6/2009 |
| WO | WO 2009118763 A1 * | 10/2009 |

OTHER PUBLICATIONS

Pubchem—"desvenlafaxine." Retrieved on Nov. 13, 2015. Retrieved from the internet <URL:http://pubchem.ncbi.nlm.nih.gov/compound/desvenlafaxine#section=Top>.*
Tiwari et al (Jul./Aug. 2009). "Applications of Complementary Polymers in HPMC Hydrophilic Extended Release Matrices." Drug Delivery Technology, 9(7): 20-27.*

* cited by examiner

*Primary Examiner* — Anoop Singh
*Assistant Examiner* — Doan Phan
(74) *Attorney, Agent, or Firm* — Bio Intellectual Property Services LLC (Bio IPS); O. (Sam) Zaghmout

(57) ABSTRACT

The present invention refers to a modified release pharmaceutical composition comprising desvenlafaxine or salts thereof, a release rate modifying system that controls the release of active agent(s) in both acidic and basic environments. A process of making and method of using the above-described composition is also disclosed.

2 Claims, No Drawings

MODIFIED RELEASE DOSAGE FORM COMPRISING DESVENLAFAXINE OR SALTS THEREOF

FIELD OF THE INVENTION

The present invention relates to modified release pharmaceutical compositions comprising desvenlafaxine or salts thereof, a release rate modifying system that controls the release of active agent in both acidic and basic environments to provide extended release of active ingredient, and optionally one or more other pharmaceutically acceptable excipient. The present invention also relates to the process for preparation of such compositions and the method of using such compositions. The pharmaceutical compositions of the present invention are useful in providing therapeutically effective levels of active agent for extended time period.

BACKGROUND OF THE INVENTION

Desvenlafaxine (O-desmethylvenlafaxine or ODV) is a selective serotonin and norepinephrine reuptake inhibitor (SNRI), is indicated for the treatment of major depressive disorder (MDD). Chemically desvenlafaxine is RS-4-[2-dimethylamino-1-(1-hydroxycyclohexyl)ethyl]phenol of formula I.

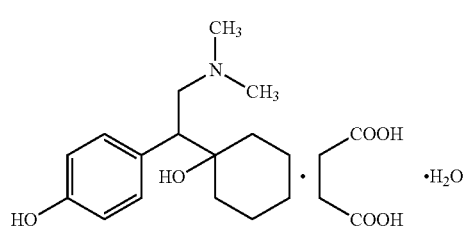

Formula I

Desvenlafaxine is marketed as PRISTIQ® in the form of extended-release tablet for oral administration that contains desvenlafaxine succinate, a structurally novel SNRI for the treatment of MDD. Desvenlafaxine is the major active metabolite of the antidepressant venlafaxine, a medication used to treat major depressive, generalized anxiety, social anxiety and panic disorders. Desvenlafaxine succinate is a white to off-white powder that is soluble in water. The solubility of desvenlafaxine succinate is pH dependent (solubility increases at lower pH). Its octanol:aqueous system (at pH 7.0) partition coefficient is 0.21 & pKa values are 8.34 (dimethylamino group) and 10.11 (phenolic group).

Desvenlafaxine was disclosed by Klamerus, K. J. et al., "Introduction of the Composite Parameter to the Pharmacokinetics of Venlafaxine and its Active O-Desmethyl Metabolite", J. Clin. Pharmacol. 32:716-724 (1992), U.S. Pat. No. 4,535,186, and as a free base in International Patent Publication No. WO 00/32555. In U.S. Pat. No. 6,673,838, ODV has been incorporated into an extended release tablet, which allegedly reduces adverse effects such as nausea, vomiting, diarrhea, and abdominal pain. The '838 patent discloses the use of hydroxypropylmethyl cellulose (HPMC) alone as a polymer to provide extended release of desvenlafaxine. However, it is known with the art that HPMC matrices may exhibit an initial burst release for soluble drugs and this behaviour has been attributed to the rapid dissolution of the drug from the surface and near the surface of the matrix.

Prior arts describing various controlled release formulation for desvenlafaxine includes U.S. Pat. Nos. 7,291,347; 6,274,171; US Application Nos. 20060193911; 20060193912; 20050175698; 20060193912; 20050244498; 20100209489; 20100330172; EP Publication Nos. 1864967; 1360169; 1711167; 2119696; 2211847 and WO Publication Nos. 2009049354; 2002064543; 2003103603; 2010090991; 2009049354.

Several attempts to provide dosage forms for delivery of desvenlafaxine or salts thereof for extended periods of time have been described previously. However, there still exists a need to develop effective modified release dosage form compositions particularly comprising desvenlafaxine or salts thereof with reduced side effects which can provide sustained delivery of desvenlafaxine or salts thereof, that are easier to manufacture, and involves a low formulation cost. Desvenlafaxine is a weakly basic drug having relatively good solubility at gastric pH and poor solubility at intestinal pH. Thus, formulating Desvenlafaxine or salts thereof into a modified release dosage form that overcomes the solubility issues of desvenlafaxine in the GIT presents a number of problems. Clearly, there is a need for improved compositions providing modified release dosage form that overcomes the solubility issues of desvenlafaxine in the GIT and provide a sustained drug release over the desired period of time to achieve the desired concentration of desvenlafaxine or salts thereof in the blood.

SUMMARY OF THE INVENTION

One of the aspects of present invention provides a modified release pharmaceutical composition comprising desvenlafaxine or salts thereof, a release rate modifying system that controls the release of active agent in both acidic and basic environments to provide extended release of active ingredient, and optionally one or more other pharmaceutically acceptable excipient.

Another aspect of present invention provides a modified release pharmaceutical composition comprising desvenlafaxine or salts thereof, a release rate modifying system that controls the release of active agent in both acidic and basic environments to provide extended release of active ingredient, wherein the release rate modifying system comprises of a combination of at least two pH independent rate controlling polymer, optionally with one or more other pharmaceutically acceptable excipient.

Another aspect of the present invention provides a process for preparation of such composition which comprises of the following steps: i) mixing the desvenlafaxine or salts thereof with release rate modifying system, ii) optionally adding one or more pharmaceutically acceptable excipient, and iii) formulating the mixture into a suitable dosage form.

Yet another aspect of present invention provides a process for the preparation of such novel composition which comprises of the following steps: i) mixing the desvenlafaxine or salts thereof with release rate modifying system, ii) granulating the mixture of step i) with suitable granulating agent, iii) mixing the granules of step ii) with one or more pharmaceutically acceptable excipient, and iv) formulating the mixture into a suitable dosage form.

In yet another aspect of the present invention provides a method of using such composition, which comprises administering to a subject in need thereof an effective amount of the composition.

Embodiments of the pharmaceutical composition may include one or more of the following features. For example, the pharmaceutically acceptable excipients may include diluents, disintegrants, binders, bulking agents, anti-adherents, anti-oxidants, buffering agents, colorants, flavoring agents, coating agents, plasticizers, stabilizers, preservatives, lubricants, glidants, chelating agents, and the like known to the art used either alone or in combination thereof.

DETAILED DESCRIPTION OF THE INVENTION

The present invention provides a modified release dosage form that overcomes the solubility issues of desvenlafaxine in the GIT and provides a sustained drug release over the desired period of time to achieve the desired concentration of desvenlafaxine or salts thereof in the blood.

In an embodiment, the present invention provides an extended release dosage form of desvenlafaxine or salts thereof; wherein desvenlafaxine is weakly basic drug, therefore have an appreciable release in stomach i.e. acidic pH environment but relatively less release in the intestine i.e. basic pH environment. Hence, the composition of the present invention is particularly useful for providing required therapeutic effects of desvenlafaxine or salts thereof, by providing appreciable release in both acidic and basic pH environments and thus being absorbed throughout the gastro-intestinal tract (GIT).

In another embodiment, the present invention provides modified release pharmaceutical composition comprising desvenlafaxine or salts thereof, a release rate modifying system that controls the release of desvenlafaxine or salts thereof in both acidic and basic environments, and optionally one or more other pharmaceutically acceptable excipient.

In an embodiment of the present invention, the release rate modifying system comprises at least two pH independent rate controlling polymer, optionally with one or more other pharmaceutically acceptable excipient.

In another embodiment, the present invention provides modified release pharmaceutical composition wherein the said system releases desvenlafaxine or salts thereof predominantly by diffusion mechanism or combination of erosion and diffusion mechanisms.

In another embodiment, the present invention provides modified release pharmaceutical composition wherein the said system releases desvenlafaxine or salts thereof predominantly by diffusion mechanism or combination of erosion and diffusion mechanisms, wherein there is no substantial deformation of shape of the dosage form during release and which provides therapeutic concentrations of desvenlafaxine or salts thereof for extended periods of time.

In yet another embodiment, the novel compositions of the present invention releases the desvenlafaxine or salts thereof for a period of about 8-24 hours, optionally having an initial lag time wherein only 0% to about 25% of active agent(s) is released, followed by a sustained release of desvenlafaxine or salts thereof.

In another embodiment, the system used for controlling release rate of the desvenlafaxine or salts thereof in the present invention comprises a release rate modifying system that controls the release of active agent in both acidic and basic environments.

The composition of the present invention is unique because the presence of atleast two pH independent polymers in the release rate modifying system contributes substantially towards the control of initial rapid drug release in acidic environment and facilitation of complete drug release in intestinal environment, wherein the release rate modifying system act by controlling the release of desvenlafaxine or salts thereof in both acidic and basic environments, enhances the intactness of the dosage form, controls the rate of erosion of the dosage form and ensures the sustained release behavior of the dosage form.

Further, in the present invention the release rate modifying system work by forming a gel layer in contact with water and thus drug dissolves within the gel layer and diffuses out into the media. Therefore, it is important to ensure the integrity of the gel layer after the drug has been dissolved and released from the gel layer. In this case, it is essential to have a strong gel layer through which diffusion can occur and hence, high viscosity of gel layer is needed in the formulation. Therefore, increase in the viscosity of the system due to presence of atleast two pH independent polymers directly affects the extended release characteristics of the oral dosage form.

In an embodiment of the present invention, the pH independent polymers are selected from but not limited to a group comprising alkyl celluloses such as methyl cellulose, hydroxyalkyl alkyl celluloses such as hydroxypropyl methyl cellulose (HPMC, HPMC® KIOOM CR, Methocel®), hydroxy alkyl celluloses such as hydroxypropyl cellulose (HPC, Klucel®) and hydroxy ethyl cellulose (HEC, Natrosol®), sodium carboxymethyl cellulose (Blanose®), polyethylene glycols (PEG®, Lutrol®), copolymers of ethylene oxide with propylene oxide (Poloxamer®), gelatin, polyvinylpyrrolidones (PVP, Kollidon®), vinylpyrrolidones, vinyl acetates, polyvinylimidazoles, polyvinylpyridine N-oxides, copolymers of vinylpyrrolidone with long-chained alpha-olefins, copolymers of vinylpyrrolidone with vinylimidazole, poly(vinylpyrrolidone/dimethylaminoethyl methacrylates), copolymers of vinylpyrrolidone/dimethylaminopropyl methacrylamides, copolymers of vinylpyrrolidone/dimethylaminopropyl acrylamides, quaternised copolymers of vinylpyrrolidones and dimethylaminoethyl methacrylates, terpolymers of vinylcaprolactam/vinylpyrrolidone/dimethylaminoethyl methacrylates, copolymers of vinylpyrrolidone and methacrylamidopropyl-trimethylammonium chloride, terpolymers of caprolactam/vinylpyrrolidone/dimethylaminoethyl methacrylates, copolymers of styrene and acrylic acid, polycarboxylic acids, polyvinyl alcohols (PVA, Mowiol®), hydrolysed polyvinyl acetate, polysaccharide gums, both natural and modified (semisynthetic), including but not limited to xanthan gum, veegum, agar, guar gum, locust bean gum, gum arabic, okra gum, benitonite, arabinoglactin, pectin, tragacanth, scleroglucan, dextran, amylose, amylopectin, dextrin, and the like, or mixtures thereof.

In another embodiment of the invention, atleast two pH independent polymers are hydroxypropyl methylcellulose and sodium carboxymethyl cellulose.

In another embodiment of the present invention, the ratio of pH independent rate controlling polymers is about 1:10 to about 10:1.

In another embodiment of the present invention, the ratio of hydroxypropyl methylcellulose and sodium carboxymethyl cellulose is about 1:10 to about 10:1.

In another embodiment, hydroxypropyl methylcellulose and sodium carboxymethyl cellulose together provide quick polymer hydration which in turn quickly initiate formation of surface gel layer in order to prevent immediate tablet disintegration and premature drug release.

Hydroxypropyl methylcellulose and sodium carboxymethyl cellulose together provide synergistic increase in viscosity, which allows erosion to occur at slower rate in order to provide extended release of drug for extended period of time.

In another embodiment, microcrystalline cellulose present in formulation is from about 1% to about 20% of the total weight of the composition.

In another embodiment, microcrystalline cellulose present in formulation is from about 10% to about 20% of the total weight of the composition.

The one or more pharmaceutically acceptable excipient of the present invention are selected from but not limited to a group comprising diluents, disintegrants, binders, bulking agents, anti-adherents, anti-oxidants, buffering agents, colorants, flavoring agents, coating agents, plasticizers, stabilizers, preservatives, lubricants, glidants, chelating agents, and the like known to the art used either alone or in combination thereof. Certain excipients used in the present composition can serve more than one purpose.

In an embodiment of the present invention, the diluent is selected from but not limited to a group comprising microcrystalline cellulose, lactose, starch, dibasic calcium phosphate, saccharides, and mixtures of the foregoing. Examples of diluents include microcrystalline celluloses (Avicel®); lactose such as lactose monohydrate, lactose anhydrous (Pharmatose®), and lactose spray dried forms; dibasic calcium phosphate (Emcompress®); mannitol (Pearlitol®); starch; sorbitol; sucrose; glucose; cyclodextrins; and the like or mixtures thereof.

In an embodiment of the present invention, suitable binders include for example starch, polyvinylpyrrolidone, hydroxypropyl methylcellulose, pregelatinised starch, hydroxypropylcellulose, or mixtures thereof. Suitable lubricants are selected from but not limited to a group comprising colloidal silicon dioxide such as Aerosil® 200, talc, stearic acid, magnesium stearate, calcium stearate, sodium stearyl fumarate, hydrogenated vegetable oil and the like, or mixtures thereof. Suitable disintegrants include for example crosslinked polyvinyl pyrrolidone, corn starch, potato starch, maize starch and modified starches, croscarmellose sodium, sodium starch glycollate, carboxymethyl cellulose calcium, or mixtures thereof.

In another embodiment of the present invention, provides a process for preparation of such composition which comprises: i) mixing the desvenlafaxine or salts thereof with release rate modifying system, ii) optionally adding one or more pharmaceutically acceptable excipient, and iii) formulating the mixture into a suitable dosage form.

In another embodiment, the composition of the present invention is formulated as a solid dosage form such as tablets/minitablets, capsules, pellets or the like.

In another embodiment, the composition of the present invention is a tablet.

In yet another embodiment, the tablets can be prepared by either wet granulation, direct compression, or by dry compression (slugging).

In another embodiment of the present invention, the oral composition is prepared by wet granulation. The granulation technique is either aqueous or non-aqueous. The non-aqueous solvent used is selected from a group comprising acetone, ethanol, isopropyl alcohol and methylene chloride.

In another embodiment, the compositions of the present invention are in the form of compressed tablets, molded tablets, mini-tablets, capsules, compacts, pellets, granules and the like. The tablets may be optionally coated with a nonfunctional coating to form a nonfunctional layer. The tablets/minitablets may be optionally filled into capsules.

In another embodiments, the composition exhibits a dissolution profile such that atleast 75% of the drug is released within 20 hours, wherein the release rate is measured in Apparatus-I (USP, Dissolution, Basket, 100 rpm) using 900 ml, 0.9% NaCl in water at 37° C.±0.5° C.

In another embodiment, the composition exhibits a dissolution profile such that at least 50% of the drug is released within 12 hours, wherein the release rate is measured in Apparatus-I (USP, Dissolution, Basket, 100 rpm) using 900 ml, 0.9% NaCl in water at 37° C.±0.5° C.

In yet another embodiment of the present invention, provides a method of using such modified release composition, which comprises administering to a subject in need thereof an effective amount of the composition.

In another embodiment, the composition of the present invention may be useful in the prevention or treatment of various central nervous system disorders including, but not limited to depression (major depressive disorder, bipolar disorder and dysthymia), fibromyalgia, anxiety, panic disorder, agoraphobia, post traumatic stress disorder, premenstrual dysphoric disorder, attention deficit disorder, obsessive compulsive disorder, social anxiety disorder, generalized anxiety disorder, autism, schizophrenia, obesity, anorexia nervosa, bulimia nervosa, Gilles de la Tourette Syndrome, vasomotor flushing, cocaine and alcohol addiction, sexual dysfunction, (including premature ejaculation), borderline personality disorder, chronic fatigue syndrome, incontinence, pain, Shy Dragger syndrome, Raynaud's Syndrome, Parkinson's Disease, epilepsy and others.

The examples given below serve to illustrate embodiments of the present invention. However they do not intend to limit the scope of present invention.

Example-1

TABLE 1

| Desvenlafaxine extended release tablet | |
|---|---|
| Ingredient | mg/tablet |
| Desvenlafaxine succinate monohydrate | 152 |
| Hypromellose 2208 (Methocel K100 MCR) | 161 |
| Sodium carboxymethylcellulose (Blanose 9M31XFPH) | 18 |
| Microcrystalline cellulose (Avicel PH 101) | 67 |
| Talc | 6 |
| Magnesium stearate | 3 |
| Opadry Pink | 11 |

Procedure

Desvenlafaxine succinate monohydrate, hypromellose, sodium carboxymethylcellulose and microcrystalline cellulose were sifted through suitable sieve. The sifted ingredients were granulated with a granulating agent in a rapid mixer granulator. The dried granules were mixed with talc in a non-shear blender and lubricated with magnesium stearate. The resulting blend was compressed. The core tablets were coated with an aqueous dispersion of Opadry.

TABLE 2

Provides the dissolution data for desvenlafaxine extended release tablet prepared as per the formula provided in Table 1 for determination of drug release rate, USP Type 1 Apparatus (rpm 100) was used wherein 0.9% NaCl in water, 900 ml was used as a medium.

| Time | Desvenlafaxine Extended Release tablet % Dissolved | Pristiq 100 mg Tablet % Dissolved |
|---|---|---|
| 1 hr | 16 | 16 |
| 2 hr | 25 | 25 |
| 4 hr | 39 | 40 |
| 6 hr | 50 | 51 |
| 8 hr | 61 | 59 |
| 10 hr | 68 | 67 |
| 12 hr | 75 | 74 |

TABLE 2-continued

Provides the dissolution data for desvenlafaxine extended release tablet prepared as per the formula provided in Table 1 for determination of drug release rate, USP Type 1 Apparatus (rpm 100) was used wherein 0.9% NaCl in water, 900 ml was used as a medium.

| Time | Desvenlafaxine Extended Release tablet % Dissolved | Pristiq 100 mg Tablet % Dissolved |
|---|---|---|
| 14 hr | 84 | 81 |
| 16 hr | 87 | 86 |
| 20 hr | 94 | 91 |
| 24 hr | 98 | 93 |

Example-2

TABLE 3

Desvenlafaxine extended release tablet

| Ingredient | % w/w |
|---|---|
| Desvenlafaxine succinate monohydrate | 20-50% |
| Hypromellose | 25-60% |
| Sodium carboxymethylcellulose | 1-10% |
| Microcrystalline cellulose | 11-20% |
| Talc | 0.5-5% |
| Magnesium stearate | 0.5-2% |
| Opadry Pink | 2-5% |

Procedure

Desvenlafaxine succinate monohydrate, hypromellose, sodium carboxymethylcellulose and microcrystalline cellulose were sifted through suitable sieve. The sifted ingredients were granulated with a granulating agent in a rapid mixer granulator. The dried granules were mixed with talc in a non-shear blender and lubricated with magnesium stearate. The resulting blend was compressed. The core tablets were coated with an aqueous dispersion of Opadry.

TABLE 4

Provides the dissolution data for desvenlafaxine extended release tablet prepared as per the formula provided in Table 3 for determination of drug release rate, USP Type 1 Apparatus (rpm 100) was used wherein 0.9% NaCl in water, 900 ml was used as a medium.
Dissolution Data for Desvenlafaxine Extended Release tablet

| Time | % Dissolved |
|---|---|
| 1 hr | 18 |
| 2 hr | 27 |
| 4 hr | 42 |
| 6 hr | 54 |
| 8 hr | 62 |
| 10 hr | 71 |
| 12 hr | 77 |
| 14 hr | 83 |
| 16 hr | 88 |
| 20 hr | 94 |
| 24 hr | 97 |

The invention claimed is:

1. A monolayered modified release pharmaceutical comprising:

| Ingredient | % w/w |
|---|---|
| Desvenlafaxine succinate monohydrate | 20-50% |
| Hypromellose | 25-60% |
| Sodium carboxy methylcellulose | 1-10% |
| Microcrystalline cellulose | 11-20% |
| Talc | 0.5-2% |
| Magnesium stearate | 0.5-5% | wherein the monolayered pharmaceutical composition is devoid of any functional coating; and
wherein the composition exhibits a dissolution profile such that at least 75% of the Desvenlafaxine is released within 20 hours, wherein the release rate is measure in Apparatus-I (USP, Dissolution, Basket, 100 rpm) using 900 ml, 0.9% NaCl in water at 37° C.±0.5° C.

2. A process of preparing the composition of claim 1, the process comprising:
i) mixing desvenlafaxine or salts thereof with hypromellose and sodium carboxy methylcellulose to form a blend;
ii) adding microcrystalline cellulose, talc and magnesium stearate to the blend of step (i); and
iii) formulating the blend of step (ii) into a suitable dosage form.

* * * * *